US006456878B1

(12) United States Patent
Yerich et al.

(10) Patent No.: US 6,456,878 B1
(45) Date of Patent: Sep. 24, 2002

(54) CARDIAC PACING SYSTEM DELIVERING MULTI-SITE PACING IN A PREDETERMINED SEQUENCE TRIGGERED BY A SENSE EVENT

(75) Inventors: Charles G. Yerich, Shoreview; Karen J. Kleckner, New Brighton; Carleen J. Juran, Shoreview, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/439,569

(22) Filed: Nov. 12, 1999

Related U.S. Application Data
(60) Provisional application No. 60/145,860, filed on Jul. 28, 1999, and provisional application No. 60/114,090, filed on Dec. 29, 1998.

(51) Int. Cl.[7] .............................................. A61N 1/362
(52) U.S. Cl. ........................................................ 607/9
(58) Field of Search ................................... 607/9, 25, 4

(56) References Cited

U.S. PATENT DOCUMENTS

| | | | |
|---|---|---|---|
| 3,937,226 A | 2/1976 | Funke | 128/419 PG |
| 4,088,140 A | 5/1978 | Rockland et al. | 128/419 PG |
| 4,332,259 A | 6/1982 | McCorkle, Jr. | 128/786 |
| 4,354,497 A | 10/1982 | Kahn | 128/419 D |
| 4,458,677 A | 7/1984 | McCorkle, Jr. | 128/786 |
| 4,548,203 A | 10/1985 | Tacker, Jr. et al. | 128/419 D |
| 4,928,688 A | 5/1990 | Mower | 128/419 PG |
| 5,123,412 A | 6/1992 | Betzold | 607/17 |
| 5,174,289 A | 12/1992 | Cohen | 128/419 PG |
| 5,267,560 A | 12/1993 | Cohen | 607/25 |
| 5,387,228 A | 2/1995 | Shelton | 607/11 |
| 5,403,356 A | 4/1995 | Hill et al. | 607/14 |
| 5,514,161 A | 5/1996 | Limousin | 607/9 |
| 5,540,727 A | 7/1996 | Tockman et al. | 607/18 |
| 5,584,867 A | 12/1996 | Limousin et al. | 607/9 |
| 5,674,259 A | 10/1997 | Gray | 607/20 |
| 5,720,768 A | 2/1998 | Verbove-Nelissen | 607/9 |
| 5,728,140 A | 3/1998 | Salo et al. | 607/9 |
| 5,741,309 A | 4/1998 | Maares | 607/9 |
| 5,792,203 A | 8/1998 | Schroeppel | 607/30 |
| 5,797,970 A | 8/1998 | Pouvreau | 607/9 |
| 5,902,324 A | 5/1999 | Thompson et al. | 607/9 |

FOREIGN PATENT DOCUMENTS

| | | | |
|---|---|---|---|
| DE | 196 15 159 | 10/1997 | A61N/1/362 |
| WO | WO 99/29368 | 6/1999 | A61N/1/37 |

OTHER PUBLICATIONS

Daubert et al., "Permanent Dual Atrium Pacing in Major Intra–atrial Conduction Blocks: A Four Years Experience", *PACE* (vol. 16, Part II, NASPE Abstract 141, p. 885, Apr. 1993).

Daubert et al., "Permanent Left Ventricular Pacing With Tranvenous Leads Inserted Into The Coronary Veins", *PACE* (vol. 21, Part II, pp. 239–245, Jan. 1998).

Cazeau et al., "Four Chamber Pacing in Dilated Cardiomyopathy", *PACE* (vol. 17, Part II, pp. 1974–1979, Nov. 1994).

Daubert et al., "Renewal of Permanent Left Atrial Pacing via the Coronary Sinus", *PACE* (vol. 15, Part II, NASPE Abstract 255, p. 572, Apr. 1992).

*Primary Examiner*—Jeffrey R. Jastrzab
(74) *Attorney, Agent, or Firm*—Girma Wolde-Michael

(57) ABSTRACT

A system for pacing in a right and its corresponding left heart chamber provides a predetermined or programmable triggered delay in a predetermined or programmable, right-to-left or left-to right sequence without first determining from which of the two chambers a triggering event originated. Devices that provide cardio defibrillation today often have pacemakers for delivering adjunct therapies, and such devices can also use the invention.

27 Claims, 8 Drawing Sheets

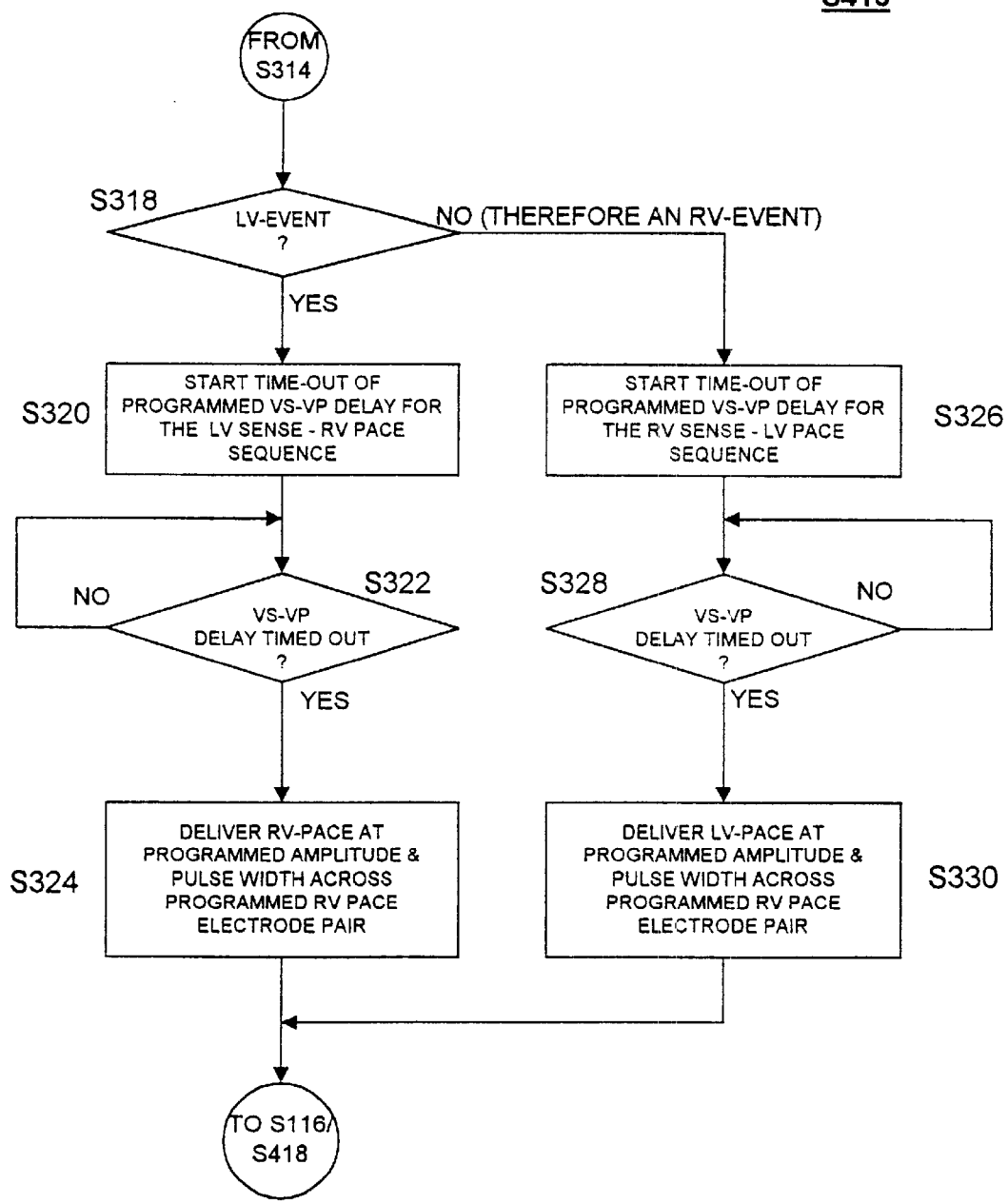

CARDIAC PACING SYSTEM DELIVERING MULTI-SITE PACING IN A PREDETERMINED SEQUENCE TRIGGERED BY A SENSE EVENT

This patent application claims the benefit of U.S. Provisional Application No. 60/114090 filed Dec. 29, 1998 and No. 60/145860 filed Jul. 28, 1999.

CROSS-REFERENCE TO RELATED APPLICATIONS

Reference is hereby made to the following, commonly assigned, copending, U.S. Patent Applications which disclose common subject matter: Ser. No. 09/067,729 filed Apr. 28, 1998 for MULTIPLE CHANNEL, SEQUENTIAL, CARDIAC PACING SYSTEMS filed in the names of C. Struble et al.; Ser. No. 09/439,244 filed on event date herewith for MULTI-SITE CARDIAC PACING SYSTEM HAVING CONDITIONAL REFRACTORY PERIOD filed in the names of K. Kleckner et al.; Ser. No. 09/439,565 filed on even date herewith for BI-CHAMBER CARDIAC PACING SYSTEM EMPLOYING UNIPOLAR LEFT HEART CHAMBER LEAD IN COMBINATION WITH BIPOLAR RIGHT HEART CHAMBER LEAD in the names of B. Blow et al.; Ser. No. 09/439,078 filed on even date herewith for MULTI-SITE CARDIAC PACING SYSTEM HAVING TRIGGER PACE WINDOW in the names of C. Juran et al.; Ser. No. 09/439,568 filed on even date herewith for RECHARGE CIRCUITRY FOR MULTI-SITE STIMULATION OF BODY TISSUE filed in the names of B. Blow et al.; and Ser. No. 09/439,243 filed on even date herewith for AV SYNCHRONOUS CARDIAC PACING SYSTEM DELIVERING MULTI-SITE VENTRICULAR PACING TRIGGERED BY A VENTRICULAR SENSE EVENT DURING THE AV DELAY in the names of C. Yerich et al.

FIELD OF THE INVENTION

The present invention pertains to multi-site cardiac pacing systems for pacing and sensing at first and second spaced apart sites of a patient's heart in triggered pacing modes in a predetermined sequence, particularly sites in right and left heart chambers.

BACKGROUND OF THE INVENTION

In diseased hearts having conduction defects and in congestive heart failure (CHF), cardiac depolarizations that naturally occur in one upper or lower heart chamber are not conducted in a timely fashion either within the heart chamber or to the other upper or lower heart chamber. In such cases, the right and left heart chambers do not contract in optimum synchrony with each other, and cardiac output suffers due to the conduction defects. In addition, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the right and left atria can result in left atrial flutter or fibrillation.

It has been proposed that various conduction disturbances involving both bradycardia and tachycardia of a heart chamber could benefit from pacing pulses applied at multiple electrode sites positioned in or about a single heart chamber or in the right and left heart chambers in synchrony with a depolarization which has been sensed at at least one of the electrode sites. It is believed that cardiac output can be significantly improved when left and right chamber synchrony is restored, particularly in patients suffering from dilated cardiomyopathy and CHF.

A number of proposals have been advanced for providing pacing therapies to alleviate these conditions and restore synchronous depolarization and contraction of a single heart chamber or right and left, upper and lower, heart chambers as described in detail in commonly assigned U.S. Pat. Nos. 5,403,356, 5,797,970 and 5,902,324 and in 5,720,768 and 5,792,203 all incorporated herein by reference. The proposals appearing in U.S. Pat. Nos. 3,937,226, 4,088,140, 4,548, 203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867, also all incorporated herein by reference.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", PACE (Vol. 16, Part II, NASPE Abstract 141, p.885, April 1993); Daubert et al., "Permanent Left Ventricular Pacing With Transvenous Leads Inserted Into The Coronary Veins", PACE (Vol. 21, Part II, pp. 239–245, January 1998); Cazeau et al., "Four Chamber Pacing in Dilated Cardiomyopathy", PACE (Vol. 17, Part II, pp. 1974–1979, November 1994); and Daubert et al., "Renewal of Permanent Left Atrial Pacing via the Coronary Sinus", PACE (Vol. 15, Part II, NASPE Abstract 255, p. 572, April 1992), all incorporated herein by reference.

Problems surface in implementing multi-site pacing in a single heart chamber or in right and left heart chamber pacing within the contexts of conventional timing and control systems. In certain circumstances, it is desirable to deliver a series of pacing pulses at spaced apart sites in a single heart chamber or in the right and left heart chamber pacing pulses as close together in time as possible upon time-out of an escape interval or synchronous AV delay or upon sensing a right or left heart chamber sense event. However, it is not always desirable to do so when pacing pulse amplitudes are programmed differently to provide for an adequate pacing threshold above the pacing amplitude sufficient to capture the heart chamber at a given pulse width. When a pacing system is implanted, the physician undertakes a work-up of the patient to determine the pacing energy and sensing thresholds that are sufficient to capture the heart and to distinguish true P-waves and R-waves from muscle artifacts and ambient electrical noise.

For example, in bi-atrial or bi-ventricular pacing systems, if left atrial pace (LA-PACE) and right atrial pace (RA-PACE) or left ventricular pace (LV-PACE) and right ventricular pace (RV-PACE) pulses are delivered simultaneously, there may be a current contribution from the highest voltage, active electrode delivering the highest voltage pulse to the lower voltage, active electrode delivering the lower voltage pulse. The contribution may be sufficient to lower the pacing threshold at the lowest voltage active electrode. Then, at a later time, the programmed mode may be changed by eliminating or lowering the voltage of the highest voltage pacing pulse, and capture may be lost at the lowest voltage active pacing electrode.

So, in these situations, at least a minimal trigger delay longer than the pacing pulse width of the first pace pulse to be delivered (PACE1) and the second pace pulse (PACE2) is necessary. In addition, the inventors have realized that determining which of the Right Heart Chamber(RHC) sense event or Left Heart Chamber(LHC) sense event has actually occurred and applying PACE1 to the corresponding pace/sense electrode adds unnecessary complexity to the pacing system and method. The inventors have realized that It is desirable and possible to simplify the sequence of delivery of PACE1 and PACE2 pulses in response to a RHC or LHC sense event without sacrificing efficacy of the triggered RHC and LHC pacing.

The inventors have also realized other applications of delivery of time pacing pulses at multiple sites of a patient's heart in one heart chamber to restore or augment a synchronous depolarization of the heart chamber.

SUMMARY OF THE INVENTION

The present invention is therefore directed to delivering at least first and second (or more) pacing pulses to first and second spaced apart sites of the heart in a predetermined sequence in response to a sensed depolarization traversing one of first and second sites, the sequence being fixed or programmed to deliver the first and second pacing pulses independently of which spaced apart site that the sensed depolarization traverses.

The method and apparatus of the present invention contemplates first and second pace/sense electrodes at first and second spaced apart sites of the heart, sensing spontaneous cardiac depolarizations traversing one of the other of the first and second pace/sense electrodes and providing a sense event signal. Upon provision of a sense event signal, a first pacing pulse is delivered to a predetermined one of the first or the second pace/sense electrodes to pace the heart at the site of that pace/sense electrode regardless of whether the sense event signal originates from a spontaneous cardiac depolarization at the first or second spaced apart sites. A triggered pacing delay is commenced and timed out on provision of the sense event signal, and a second pacing pulse is delivered to the other of the first or the second pace/sense electrodes to pace the heart at the site of that pace/sense electrode. A synchronized depolarization of the heart in a predetermined sequence is effected by the first and second pacing pulses.

In RHC and LHC pacing systems and methods of operation, the present invention provides efficient pacing of the RHC and LHC separated by a predetermined triggered delay in a predetermined, programmed or fixed, right-to-left or left-to-right sequence without determining the origin of a RHC or LHC sense event or necessarily employing separate RHC and LHC sense amplifiers.

When separate RHC and LHC sense amplifiers are provided, the present invention provides methods and apparatus for initiating triggered pacing of the RHC and LHC separated by the predetermined triggered delay in the predetermined right-to-left or left-to-right sequence upon either a RHC or LHC sense event.

A single sense amplifier can be coupled to a sense electrode pair situated in relation to the RHC or LHC or traversing the RHC and LHC. In this case, the present invention provides methods and apparatus for initiating triggered pacing of the RHC and LHC separated by the predetermined triggered delay in the predetermined right-to-left or left-to-right sequence upon RHC or LHC or RHC-LHC sense event.

In a bi-chamber pacing system, an IPG optionally having an indifferent IPG can electrode is coupled to a small diameter, unipolar, LHC endocardial lead and a bipolar RHC endocardial lead. The LHC lead is advanced through a venous pathway to locate the LHC active pace/sense electrode at a desired LHC pace/sense site. The RHC lead is advanced into the RHC chamber to locate RHC active and indifferent pace/sense electrodes therein. Sensing of RHC spontaneous cardiac depolarizations to provide a RHC sense event signal and delivery of RHC pacing pulses is conducted across the RHC active pace/sense electrode and one of the RHC or IPG indifferent pace/sense electrodes. Sensing of LHC spontaneous cardiac depolarizations to provide a LHC sense event signal is conducted across the LHC active pace/sense electrode and one of the RHC active or indifferent pace/sense electrodes or the IPG indifferent can electrode. Delivery of LHC pacing pulses is preferably conducted across the LHC active pace/sense electrode and the RHC indifferent pace/sense electrode, whereby the LHC pacing vector traverses the mass of the LHC.

In a bi-ventricular pacing system, a small diameter, unipolar, left ventricular, coronary sinus (LV CS) endocardial lead and a bipolar right ventricular (RV) endocardial lead are preferably employed to provide the LHC and RHC pace/sense electrodes. In a bi-atrial pacing system, a unipolar, left atrial, coronary sinus (LA CS) lead and a bipolar right atrial (RA) endocardial lead are preferably employed to provide the LHC and RHC pace/sense electrodes. Epicardial leads may be used also, or even bi-polar LV leads or ICD (Implantable CardioDefibrilator) patch electrodes where available and desireable.

The present invention is preferably implemented in pacing systems for providing atrial or ventricular bi-chamber pacing or AV synchronous pacing systems for providing three or four chamber pacing.

The present invention is preferably implemented into an external or implantable pulse generator and lead system selectively employing right and left heart, atrial and/or ventricular leads. The preferred embodiment is implemented in an architecture that allows wide programming flexibility for operating in AV synchronous modes with right and left ventricular pacing or in atrial or ventricular only modes for providing only right and left atrial or ventricular pacing. The AV synchronous embodiments may be implemented into an IPG or external pulse generator and lead system providing right and left ventricular pacing and sensing and either both right and left atrial pacing or just right or left atrial pacing and sensing. Alternatively, the invention can be implemented in IPGs or external pulse generators and lead systems having hard wired connections and operating modes that are not as programmable.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 6A–6B is a flow chart illustrating the steps of delivering ventricular pacing pulses following a ventricular sense event during the time-out of an AV delay or the V-A escape interval in FIG. 4.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIGS. 4 through 6A–6B for restoring synchrony in depolarizations and contraction of left and right ventricles in synchronization with atrial sensed and paced events for treating bradycardia in those chambers. This embodiment of the invention is programmable to operate as a three or four channel pacing system having an AV synchronous operating mode for restoring upper and lower heart chamber synchronization and right and left atrial and/or ventricular chamber depolarization synchrony. But, it will be realized that the invention can also be practiced in a bi-ventricular or bi-atrial pacing system that can be dedicated to such use or can be a programmable mode of the system of FIGS. 2 and 3 following the flow chart of FIG. 7. The invention can be practiced in a two channel or four channel pacing system of the type disclosed in the above-incorporated '324 patent as well. Moreover, the invention can be practiced in a pacemaker providing pacing and sensing at multiple spaced apart pace/sense electrode sites in a single heart chamber following the steps of FIG. 7.

It should be appreciated that the present invention may be utilized particularly to treat patients suffering CHF with or without bradycardia. The pacing system of the present invention may also may be incorporated into an anti-tachyarrhythmia system including specific high rate pacing and cardioversion shock therapies for providing staged therapies to treat a diagnosed arrhythmia.

Figure 1:
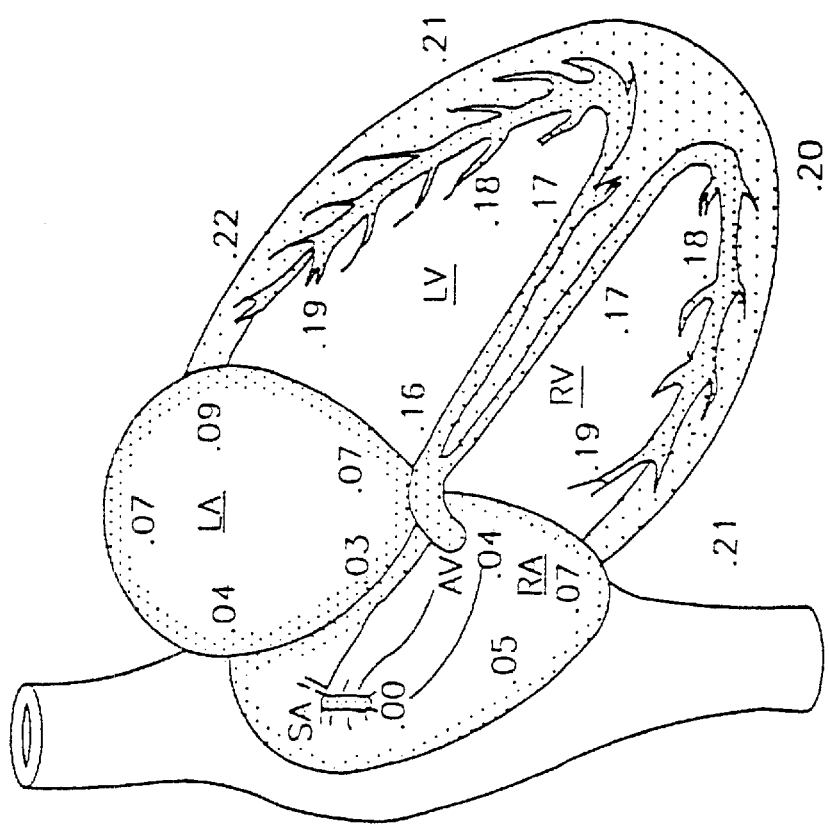
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the cardiac veins. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying repolarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak-peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with a first embodiment of the present invention, a method and apparatus is provided to restore the depolarization sequence of FIG. 1 and the synchrony between the right and left ventricular heart chambers that contributes to adequate cardiac output. This restoration is effected through providing optimally timed cardiac pacing pulses to the right and left ventricles as necessary and to account for the particular implantation sites of the pace/sense electrodes in relation to each heart chamber while maintaining AV synchrony. The present invention efficiently provides pacing of the RHC and LHC separated by a predetermined, i.e., a programmed or fixed, triggered delay in a predetermined, i.e., programmed or fixed, right-to-left or left-to-right sequence without determining the origin of a RHC or LHC sense event or necessarily employing separate RHC and LHC sense amplifiers.

Figure 2:
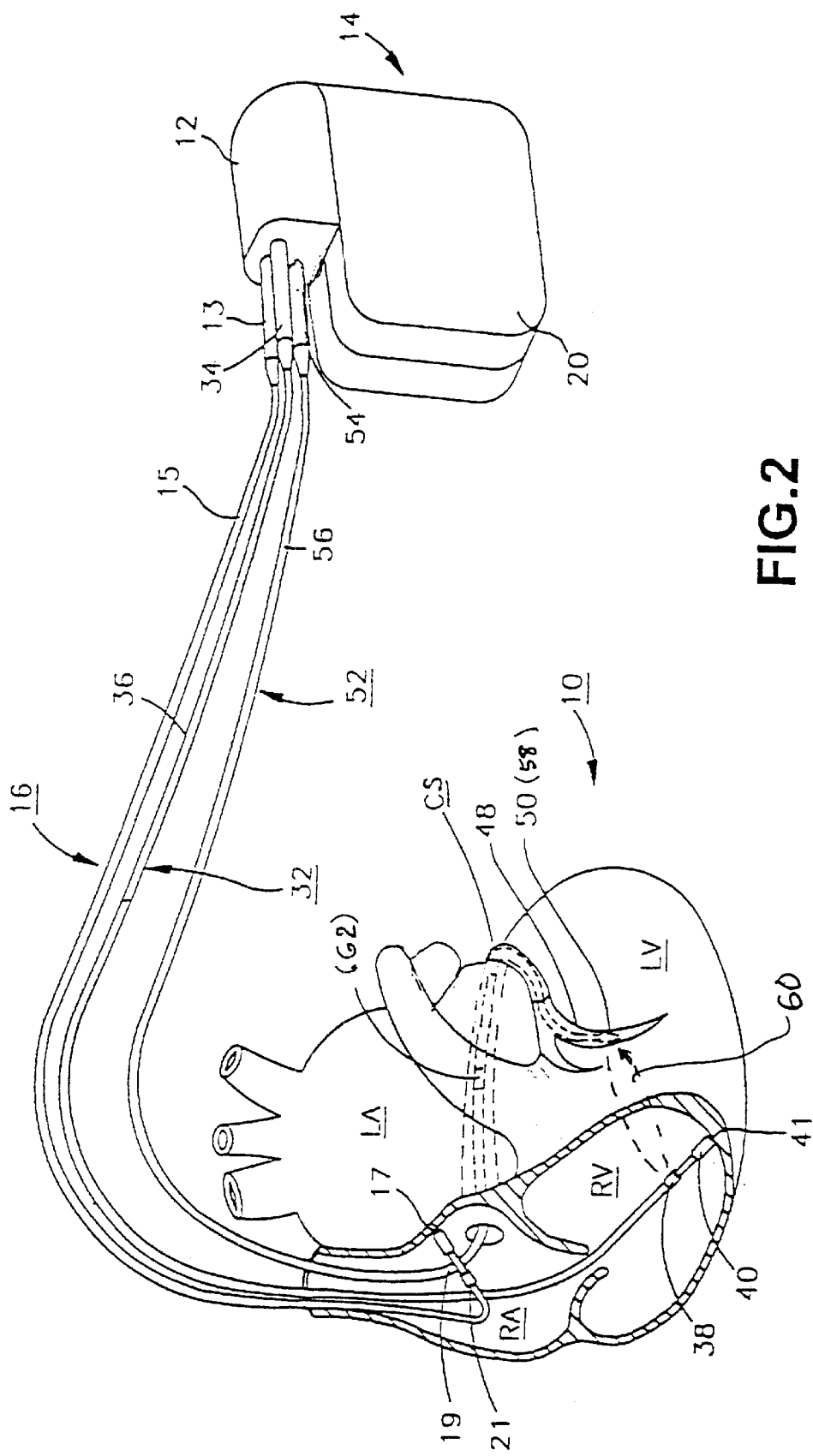
FIG. 2 is a schematic diagram depicting a three channel, atrial and biventricular, pacing system in which the present invention is preferably implemented.

FIG. 2 is a schematic representation of an implanted, three channel cardiac pacemaker of the above noted types for restoring AV synchronous contractions of the atrial and ventricular chambers and simultaneous or sequential pacing of the right and left ventricles. The Implantable Pulse Generator IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a unipolar, endocardial LV CS lead 52 is passed through a vein and the RA chamber of the heart 10, into the CS and then inferiorly in a branching vessel of the great vein 48 to extend the distal LV CS pace/sense electrode 50 alongside the LV chamber. The distal end of such LV CS leads is advanced through the superior vena cava, the right atrium, the ostium of the coronary sinus, the coronary sinus, and into a coronary vein descending from the coronary sinus. Typically, LV CS leads and LA CS leads do not employ any fixation mechanism and instead rely on the close confinement within these vessels to maintain the pace/sense electrode or electrodes at a desired site.

The LV CS lead 52 is formed with a small diameter single conductor lead body 56 coupled at the proximal end connector 54 fitting into a bore of IPG connector block 12. A small diameter unipolar lead body 56 is selected in order to place the distal LV CS pace/sense electrode 50 in a vein branching inferiorly from the coronay sinus vein 48. (Use of an epicardial lead instead is not ruled out by this discussion, and in some situations may be preferred to the CS lead).

Preferably, the distal, LV CS active pace/sense electrode 50 is paired with the proximal ring RV indifferent pace/sense electrode 38 for delivering LV pace pulses across the bulk of the left ventricle and the intraventricular septum. The distal LV CS active pace/sense electrode 50 is also preferably paired with the distal tip RV active pace/sense electrode 40 for sensing across the RV and LV as described further below.

Moreover, in a four chamber embodiment, LV CS lead 52 could bear a proximal LA CS pace/sense electrode positioned along the lead body to lie in the larger diameter coronary sinus CS adjacent the LA. In that case, the lead body 56 would encase two electrically insulated lead conductors extending proximally from the more proximal LA CS pace/sense electrode(s) and terminating in a bipolar connector 54. The LV CS lead body would be smaller between the proximal LA CS electrode and the distal LV CS active pace/sense electrode 50. In that case, pacing of the RA would be accomplished along the pacing vector between the active proximal LA CS active electrode and the proximal ring RA indifferent pace/sense electrode 21.

Figure 3:
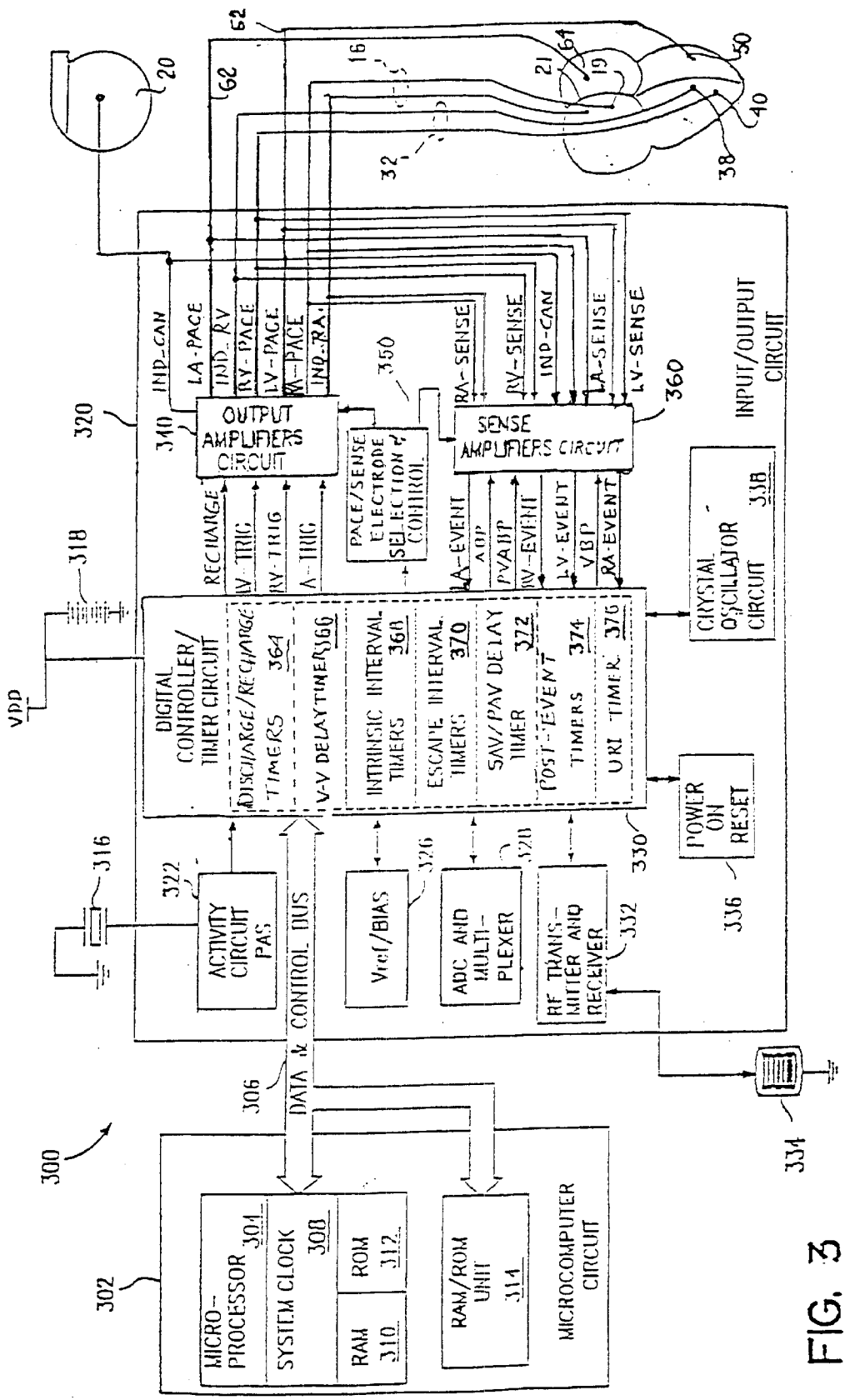
FIG. 3 is a simplified block diagrams of one embodiment of IPG circuitry and associated leads employed in the system of FIG. 2 for providing four pacing channels that are selectively programmed in bi-atrial and/or bi-ventricular pacing modes.

FIG. 3 depicts bipolar RA lead 16, optional unipolar LA lead 62, bipolar RV lead 32, and unipolar LV CS lead 52 coupled with an IPG circuit 300 having programmable modes and parameters and a telemetry transceiver of a DDDR type known in the pacing art. A unipolar LA pace/sense electrode 64 is provided at the distal end of the LA CS lead 62. The unipolar LA lead 62 may also be a CS lead and may be formed as part of the LV CS lead 52 as described above. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, and the sense amplifiers circuit 360, as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the implantable pulse generator housing 118 and may take the form of a piezoelectric crystal transducer as is well known in the art and its output signal is processed and used as the RCP. A timed interrupt, e.g., every two seconds, may be provided in order to allow the microprocessor 304 to analyze the output of the activity circuit PAS 322 and update the basic V-A (or A-A or V-V) escape interval employed in the pacing cycle.

Data transmission to and from the external programmer is accomplished by means of the telemetry antenna 334 and an associated RF transmitter and receiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-PACE, RV-PACE, LV-PACE signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include discharge/recharge timers 364, V-V delay timer 366, an intrinsic interval timer 368 for timing elapsed V-EVENT to V-EVENT intervals or V-EVENT to A-EVENT intervals, escape interval timers 370 for timing A-A, V-A, and/or V-V pacing escape intervals, an AV delay interval timer 372 for timing an AV delays from a preceding A-EVENT (SAV) or A-PACE (PAV), a post-ventricular timer 374 for timing post-ventricular time periods, and an upper rate interval (URI) timer 376. RHC pace trigger and sense events are typically used for starting and resetting these intervals and periods. However, it would be possible to allow the physician to select and program LHC pace trigger and sense events for these timing purposes.

Microcomputer 302 controls the operational functions of digital controller/timer circuit 330, specifying which timing intervals are employed, and setting at least the programmed-in base timing intervals, via data and control bus 306. Digital controller/timer circuit 330 starts and times out these intervals and delays for controlling operation of the atrial and ventricular sense amplifiers in sense amplifiers circuit 360 and the atrial and ventricular pace pulse generators in output amplifiers circuit 340.

The post-event timers 374 time out the post-ventricular time periods following an RV-EVENT or LV-EVENT or a RV-PACE or LV-PACE and postatrial time periods following an A-EVENT or A-PACE. The durations of the post-event time periods may also be selected as programmable parameters stored in the microcomputer 302. The post-ventricular time periods include the PVARP, a post-atrial ventricular blanking period (PAVBP), a ventricular blanking period (VBP), a ventricular refractory period (VRP), and a conditional ventricular refractory period (CVRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-PACE.

It should be noted that the starting of the post-atrial time periods and the AV delays can be commenced substantially simultaneously with the start or end of the A-EVENT or A-PACE. Similarly, the starting of the post-ventricular time periods and the V-A escape interval can be commenced substantially simultaneously with the start or end of the V-EVENT or V-PACE.

The microprocessor 304 also optionally calculates AV delays, post-ventricular time periods, and post-atrial time periods which vary with the sensor based escape interval established in response to the RCP(s) and/or with the intrinsic atrial rate. The variable AV delays are usually derived as a fraction of a maximum AV delay set for the pacing lower rate (i.e., the longest escape interval).

The output amplifiers circuit 340 contains a RA pace pulse generator, a LA pace pulse generator, a RV pace pulse generator and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of an AV delay provided by AV delay interval timer 372. Similarly, in order to trigger a right or left atrial pacing or RA-PACE pulse or LA-PACE pulse, digital controller/timer circuit 330 generates an RA-TRIG or LA-TRIG signal at the end of the V-A escape interval timed by escape interval timers 370.

Typically, in pacing systems of the type illustrated in FIGS. 2 and 3, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pacing pulses along pacing and sensing vectors. Separate or shared indifferent pace and sense electrodes can also be designated in pacing and sensing functions. For convenience, the following description separately designates pace and sense electrode pairs where a distinction is appropriate.

The output amplifiers circuit 340 includes switching circuits for coupling selected pace electrode pairs from among the lead conductors and the IND_CAN electrode 20 to the RA pace pulse generator, LA pace pulse generator, RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing as described below.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pacing pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier, LA sense amplifier, RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier, LA sense amplifier, RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

In accordance with one embodiment of the present invention, sensing of RHC (RA and/or RV) spontaneous cardiac depolarizations to provide a RHC sense event signal (RA-SENSE and/or RV-SENSE) and delivery of RHC pacing pulses (RA-PACE and/or RV-PACE) is conducted across the RHC active pace/sense electrode (9 and/or 40) and one of the RHC indifferent ring, pace/sense electrodes (21 and/or 38) or IPG indifferent pace/sense electrodes (IND_CAN 20). Sensing of LHC spontaneous cardiac depolarizations (LA-SENSE and/or LV-SENSE) to provide a LHC sense event signal (LA-EVENT and/or LV-EVENT) is conducted across the LHC active pace/sense electrode and one of the RHC active or indifferent pace/sense electrodes or the IPG indifferent can electrode. Delivery of LHC pacing pulses (LA-PACE and/or LV-PACE) is conducted across the LHC active pace/sense electrode (64 and/or 50) and the RHC indifferent ring pace/sense electrode (21 and/or 38), whereby the LHC pacing vector traverses the mass of the LHC.

Advantageously, the pacemaker of FIG. 3 could be simplified by providing only a single atrial sense amplifier coupled to a trans-atrial sense electrode pair comprising the active CS LA and the active RA pace/sense electrodes 64 and 19. Then, only a single A-EVENT would be provided and employed, and it may reflect either a RA-SENSE or a LA-SENSE. Similarly, the pacemaker could be simplified by providing only a single ventricular sense amplifier coupled to the collective sense electrode pair comprising the active CS LV and the active distal tip RV pace/sense electrodes 50 and 40. Then, only a single V-EVENT would be provided and employed, and it may reflect either a RV-SENSE or a LV-SENSE.

Epicardial active fixation leads may also be used and can provide for maor than one electrode for a LHC if desired, or a CS lead using more than one electrode can be used if desired. Even ICD patch electrodes can provide suitable functionality for this invention if advantageous in a particular situation.

However configured, the pacing of the RA and LA can be separated by a predetermined triggered delay in a predetermined right-to-left or left-to-right sequence, commenced on any sense event without having to prescribe the sequence depending on a determination as to which location senses the depolarization first.

Similarly, a single ventricular sense amplifier could be provided that is coupled to the active tip right and left ventricular sense electrodes 40 and 50 for sensing a collective V-EVENT. However configured, the pacing of the RV and LV separated by a predetermined triggered delay in a predetermined right-to-left or left-to-right sequence is commenced on the collective V-EVENT or on a RV-EVENT or LV-EVENT without having to prescribe the sequence depending on a determination as to which is sensed first.

To simplify the description of FIGS. 4 through 6A–6B, it will be assumed that the following references to an "A-EVENT" and "A-PACE" will be the RA-EVENT and RA-PACE, respectively, if there is no LA pacing or sensing provided or programmed on, or will be a programmed one of the RA-EVENT or LA-EVENT and RA-PACE or LA-PACE, respectively. The A-EVENT could also be the output sense event signal of the single atrial sense amplifier coupled to active pace/sense electrodes 19 and 64.

Figure 4:
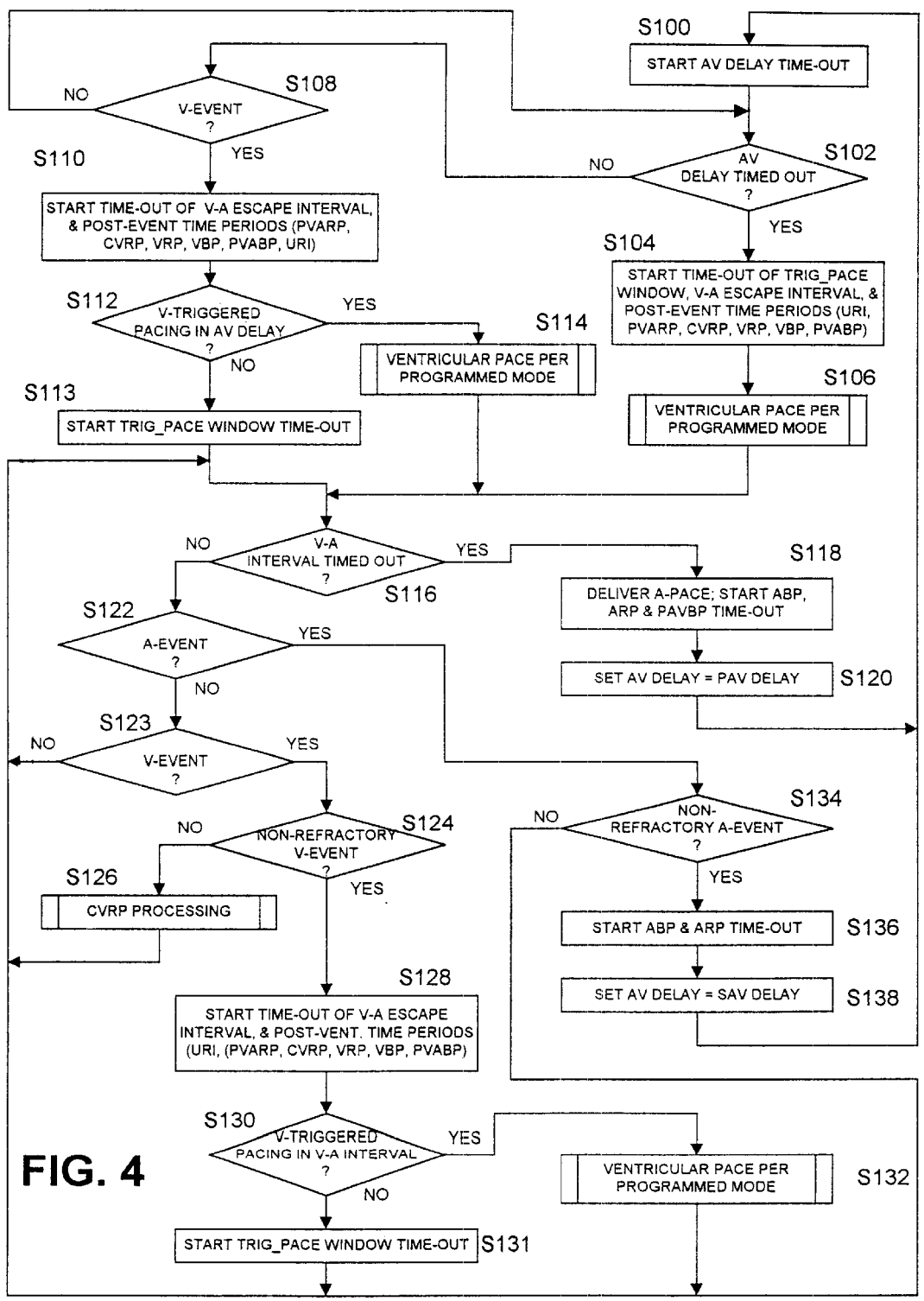
FIG. 4 is a comprehensive flow-chart illustrating the operating modes of the IPG circuitry of FIG. 3 in a variety of AV synchronous, bi-ventricular pacing modes in accordance with one embodiment of the invention.

The general operation of IPG circuit 300 is depicted in the flow chart of FIG. 4. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

The post-event timers 374 are started to time out the post-ventricular time periods and the TRIG_PACE window, and the V-A escape interval timer 370 is started to time out the V-A escape interval in step S104 if the SAV or PAV delay times out in step S102 without the detection of a non-refractory RV-EVENT or LV-EVENT. The TRIG_PACE window inhibits triggered pacing modes in response to a sense event occurring too early in the escape interval and is described in greater detail in the above-referenced Ser. No. 09/439,078 application.

Figure 5:
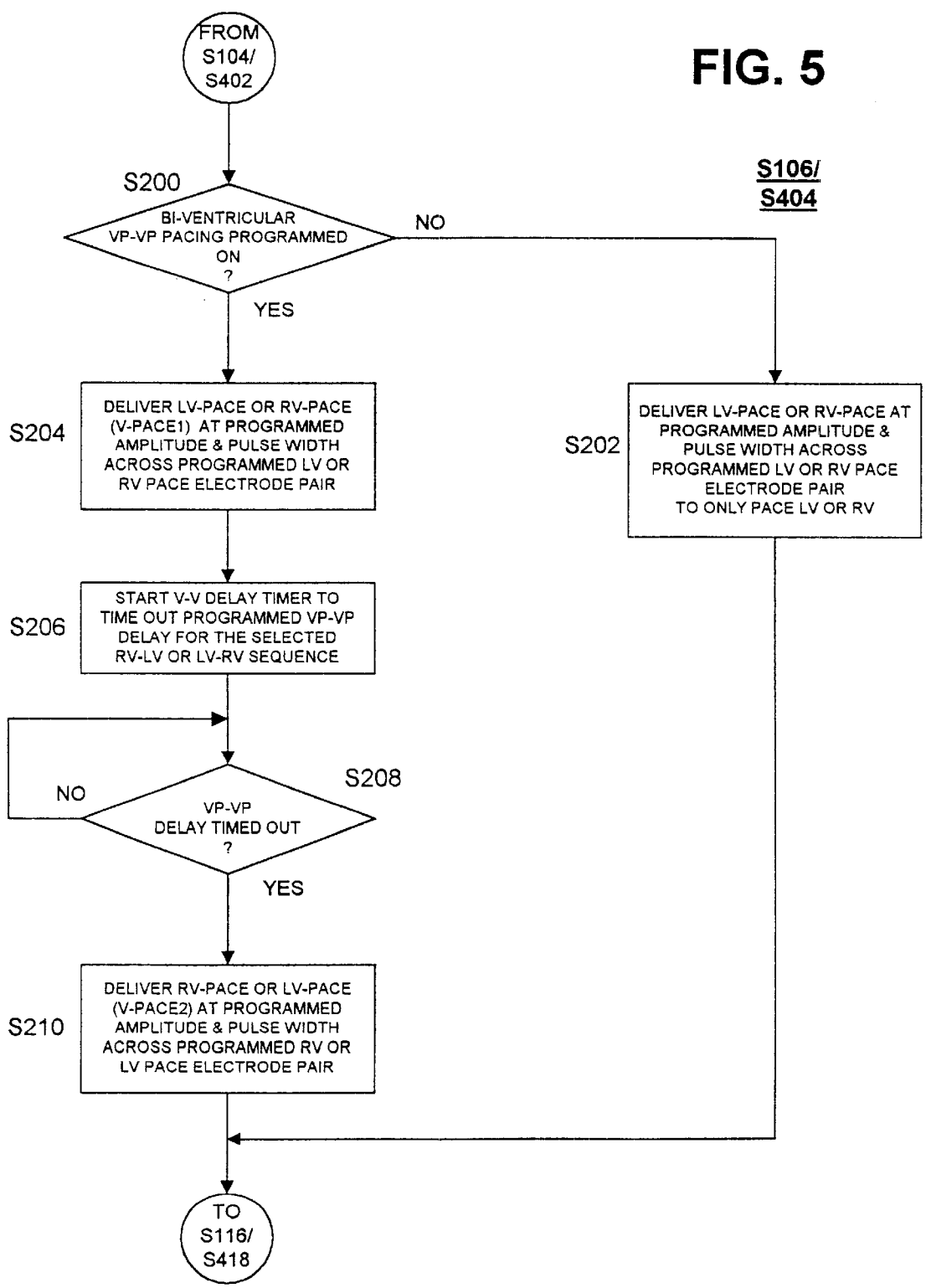
FIG. 5 is a flow chart illustrating the steps of delivering ventricular pacing pulses following time-out of an AV delay in FIG. 4.

Either a programmed one or both of the RV-PACE and LV-PACE pulses are delivered in step S106 (as shown in FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pacing pulses are separated by separately programmed VP-VP delays. The VP-VP delays are preferably programmable between nearly 0 msec and about 80 msec.

Figure 6A:
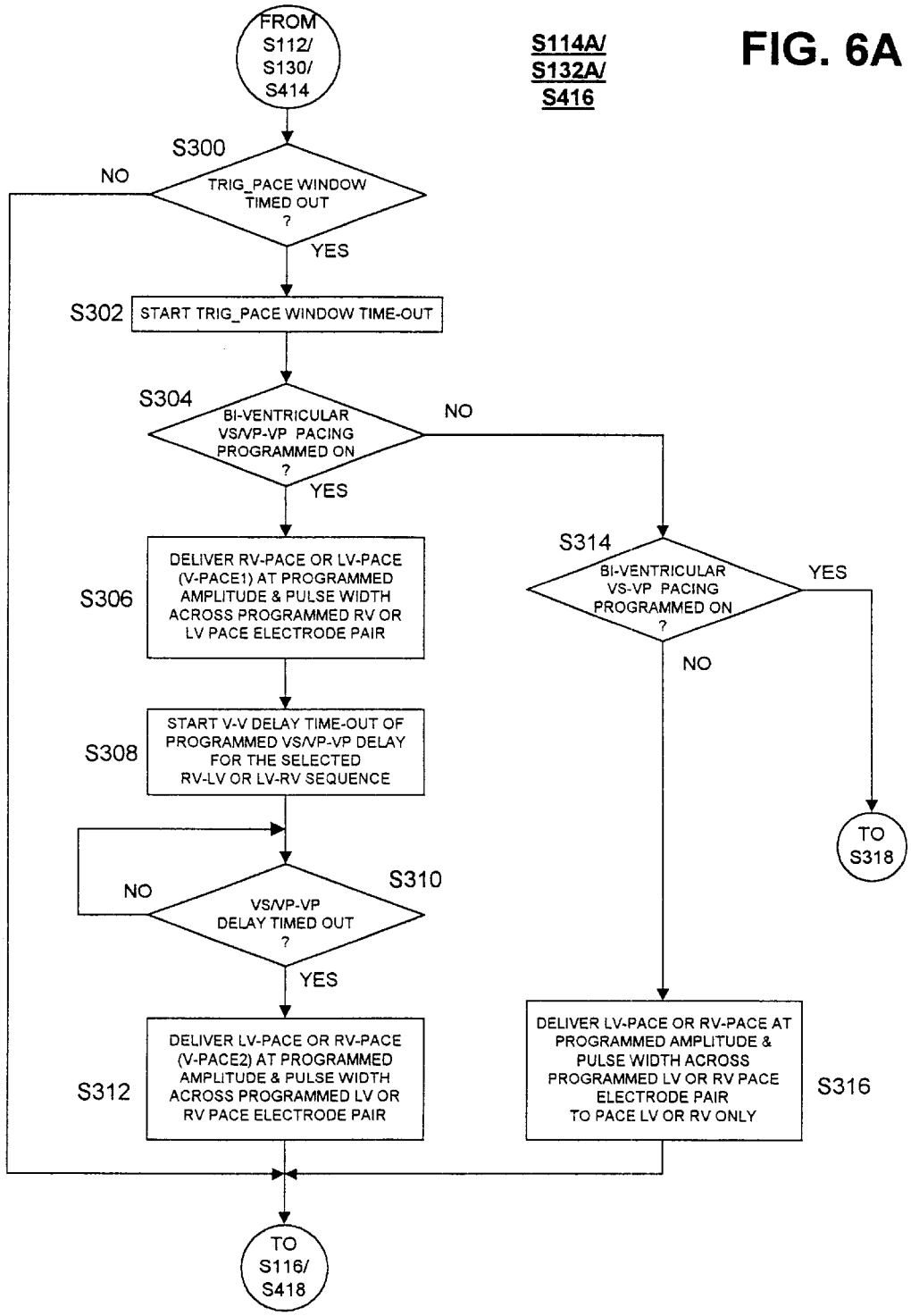

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. If one is programmed on, then it is undertaken and completed in step S114 (FIGS. 6A–6B). If a ventricular triggered pacing mode is not programmed on as determined in step S112, then no ventricular pacing is triggered by a sensed non-refractory V-EVENT terminating the AV delay. The time-out of the TRIG_PACE window is commenced in step S113 simultaneously with the time-out of the V-A escape interval and post-event time periods in step S110.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118, the AV delay is set to PAV in step S120, and the AV delay is commenced by AV delay timer 372.

If a non-refractory A-EVENT is generated as determined in steps S122 and S134, then the V-A escape interval is terminated. The ABP and ARP are commenced by post-event timers 374 in step S136, the AV delay is set to the SAV in step S138, and the SAV delay is started in step S100 and timed out by SAV/PAV delay timer 372.

Assuming that the normal activation sequence is sought to be restored, a programmed SAV and PAV delay corresponding to a normal AV conduction time from the AV node to the bundle of His are used or a calculated SAV and PAV delay is calculated in relation to the prevailing sensor rate or sensed intrinsic heart rate and are used by SAV/PAV delay timer 372.

If an RV-EVENT or LV-EVENT or a collective V-EVENT sensed across the RV tip sense electrode and the LV sense electrode (for simplicity, all referred to as a V-EVENT) is detected in step S123 during the time-out of the V-A escape interval, then, it is determined if it is a non-refractory V-EVENT or a refractory V-EVENT in step S124. If the V-EVENT is determined to be a refractory V-EVENT in step S124, then it is employed in the CVRP processing step S126 which is described in detail in the above-referenced Ser. No. 09/439,244 application. If the V-EVENT is determined to be a non-refractory V-EVENT in step S124, then the V-A escape interval is restarted, and the post-ventricular time periods are restarted in step S128.

In step S130, it is determined whether a triggered pacing mode is programmed to be operative during the V-A escape interval. If one is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval. The time-out of the TRIG_PACE window is commenced in step S131 simultaneously with the time-out of the V-A escape interval and post-event time periods in step S128.

FIG. 5 depicts the step S106 in greater detail, and FIGS. 6A–6B depict the steps S114 and S132 in greater detail. As described in greater detail below, if a VP-VP pacing mode is programmed on in step S106, it can be selectively programmed in a left-to-right or right-to-left ventricle sequence, wherein the first and second delivered ventricular pacing pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec.

As a practical matter, the minimum VS/VP-VP, and VP-VP delays may be set to one half the system clock cycle in order to avoid simultaneous delivery of RV-PACE and LV-PACE pulses. The pacing pulse width is typically programmable between about 0.5 msec and 2.0 msec, and the pacing pulse amplitude is typically programmable between 0.5 and 7.5 volts. The system clock provides a full clock cycle of about 8.0 msec. Therefore, the minimum VP-VP delay is set at a half clock cycle or about 4.0 msec.

It is desired to be able to deliver RV-PACE and LV-PACE pulses that differ from one another in pulse width and amplitude in order to make certain that the delivered energy is sufficient to capture the heart chamber without being unduly wasteful of energy. But, if differing amplitude and pulse width RV-PACE and LV-PACE pulses are simultaneously delivered to the right and left ventricles, then DC current pathways can develop between the active electrodes that can cause aberrant conduction pathways in the heart and can lead to oxidation or other deterioration of the pace/sense electrodes.

As set forth above, when a pacing system is implanted, the physician undertakes a work-up of the patient to determine the pacing energy and sensing thresholds that are sufficient to capture the heart and to distinguish true P-waves and R-waves from muscle artifacts and ambient electrical noise. If LV-PACE and RV-PACE pulses are delivered simultaneously, there may be a current contribution from the highest voltage active electrode delivering the highest voltage pulse to the lower voltage active electrode delivering the lower voltage pulse. The contribution may be sufficient to lower the pacing threshold at the lowest voltage active electrode. Then, at a later time, the programmed mode may be changed by eliminating or lowering the voltage of the highest voltage pacing pulse, and capture may be lost at the lowest voltage active pacing electrode.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP-VP delay timed out by V-V delay timer 366. If delivery of only a single RV-PACE or LV-PACE is programmed as determined in step S200, then it is delivered in step S202.

In one preferred embodiment, the LV-PACE pulse is delivered across the active LV pace electrode 50 and the indifferent ring RV (IND_RV) pace electrode 38 in a trans-ventricular pacing path 60 (shown schematically in FIG. 2) encompassing the bulk of the LV and intraventricular septum separating the pace/sense electrodes. Although the active RV pace electrode 40 could be programmed to be paired as the indifferent electrode with the active LV pace electrode 50 it is generally not desirable to do so since both are of relatively small surface area, and it is usually desirable to provide a relatively large indifferent electrode surface area to function as an anode. Other pacing pathways become available is another LV electrode is available, or if using a larger one as would be available with a patch electrode, and these could be used as well.

If VP-VP pacing is programmed on in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected through the pace/sense electrode selection and control 350 depending upon which are present in the pacing system and the RV pacing vector that is desired as set forth above. And, the LV-PACE pulse is delivered across the active LV pace electrode 50 and the IND_RV pace electrode 38 in the trans-ventricular pacing path 60. The V-PACE1 pacing pulse is delivered at a programmed pulse energy dictated by the programmed voltage and pulse width.

The V-V delay timer 366 is loaded with the programmed VP-VP delay and starts to time out in step S206. If the RV-PACE pulse is V-PACE1, then a programmed VP-VP delay is timed in V-V delay timer 366. The LV-PACE pulse is delivered as V-PACE2 in the LV pacing path 60 between the active LV pace electrode 50 and IND_RV pace electrode 38 in step S210 after time-out of the programmed VP-VP delay in step S208. Conversely, if the LV-PACE pulse is the first to be delivered (V-PACE1) in the pacing path 60, then a programmed VP-VP delay is timed in V-V delay timer 366. The RV-PACE pulse is then delivered as V-PACE2 typically across the active RV pace electrode 40 and the programmed indifferent electrode in step S210 after time-out of the programmed VP-VP delay in step S208.

FIG. 6A–6B is a flow chart illustrating the steps S112 and S132 of FIG. 4 for delivering ventricular pacing pulses triggered by a ventricular sense event in step S108 during the time-out of an AV delay or in step S124 during time-out of the V-A escape interval. As noted above, the sensing of R-waves in the RV and LV can be accomplished employing several RV-SENSE and LV-SENSE sensing axes or vectors and the trans-ventricular sensing vector. A bipolar RV-SENSE vector (RV sense electrodes 38 and 40), a unipolar RV-SENSE vector (RV tip sense electrode 40 and IND_CAN electrode 20), and a unipolar LV-SENSE vector (LV sense electrode 50 and IND_CAN electrode 20), and a trans-ventricular, combined RV-SENSE and LV-SENSE vector (RV tip sense electrode 40 and LV sense electrode 50) can be programmed. The selection of the sensing vectors would depend upon heart condition and the selection of the pacing pulse pathways.

The IPG circuit 300 can be separately programmed in one of three triggered pacing modes designated VS/VP, VS/VP-VP or VS-VP triggered modes for each of steps S114 and S132. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP-VP delay times out. In the VS-VP pacing mode, a RV-EVENT or the LV-EVENT starts time-out of a VS-VP delay, and a single pacing pulse (designated V-PACE2) is delivered to the selected LV or the RV pace electrode pair, respectively, when the VS-VP delay times out. The VS-VP pacing mode is not employed in the practice of the present invention and could be eliminated from the IPG, but is described for completeness of the disclosure of an embodiment in which the present invention can be incorporated.

The TRIG_PACE time window started by a prior V-EVENT or V-PACE must have timed out in step S300 prior to delivery of any triggered ventricular pacing pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP-VP triggered mode as determined in step S304, the non-refractory RV-EVENT or LV-EVENT or collective V-EVENT event of indeterminable origin is treated as a single V-EVENT. If the TRIG PACE_window has timed out as determined in step S300, then the single V-EVENT triggers the immediate delivery of a programmed one of the RV-PACE or a LV-PACE as V-PACE1 across the programmed bipolar or unipolar RV and LV pace electrode pair, respectively, in step S306. Thus, V-PACE1 is delivered to a predetermined RV or LV pace electrode pair, regardless of whether a RV-EVENT and LV-EVENT is sensed.

Then, a VS/NP-VP delay is started in step S308 and timed out in step S310. The VS/NP-VP delay is specified as a VP-VP delay when the RV-PACE is V-PACE1 and the LV-PACE is V-PACE2. The VS/VP-VP delay is specified as a VP-VP delay when the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In the simplest embodiment of the present invention, the VS/NP-VP mode would be the only triggered ventricular pacing mode provided. The remaining steps of FIGS. 6A and 6B are described in the event that the VS/VP and/or the VS-VP triggered ventricular pacing mode is included in the pacing system.

In step S314, it is determined whether the VS-VP triggered pacing mode or the VS/VP triggered pacing mode is programmed. When the IPG circuit 300 is programmed to a single heart chamber VS/VP triggered pacing mode, the RV-EVENT or LV-EVENT triggers the immediate delivery of an RV-PACE or an LV-PACE across a programmed bipolar or unipolar RV or LV pace electrode pair, respectively, in step S316, regardless of whether an RV-EVENT or LV-EVENT was sensed.

When the IPG circuit 300 is programmed to the VS-VP triggered pacing mode, an LV-EVENT as determined in step S318 loads the appropriate VS-VP delay in V-V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer 366 in step S326 and the VS-VP delay is timed out in step S328. The LV-PACE (also designated V-PACE2) is delivered at time-out of the VS-VP delay in step S330.

The V-A escape interval is timed out in step S116 following the completion of the ventricular pacing mode of FIGS. 6A–6B for steps S114 and S132. If the V-A escape interval times out, then an RA pace pulse is typically first delivered across the RA pace electrodes 17 and 19 in step S118, and the AV delay timer is restarted in step S100.

In all of steps S306, S312, S316, S324 and S330, the LV-PACE pulse, if delivered through a unipolar CS lead is delivered as V-PACE2 in the LV pacing path 60 between the active LV pace electrode 50 and IND_RV pace electrode 38, and with other leads may be delivered along other pathways as desired.

The present invention may also be advantageously implemented in many of the bi-chamber pacing systems described above, e.g. those described in the above-incorporated '324 patent, or a single chamber pacemaker having two or more pace/sense electrodes located at spaced apart sites in the single heart chamber.

Figure 7:
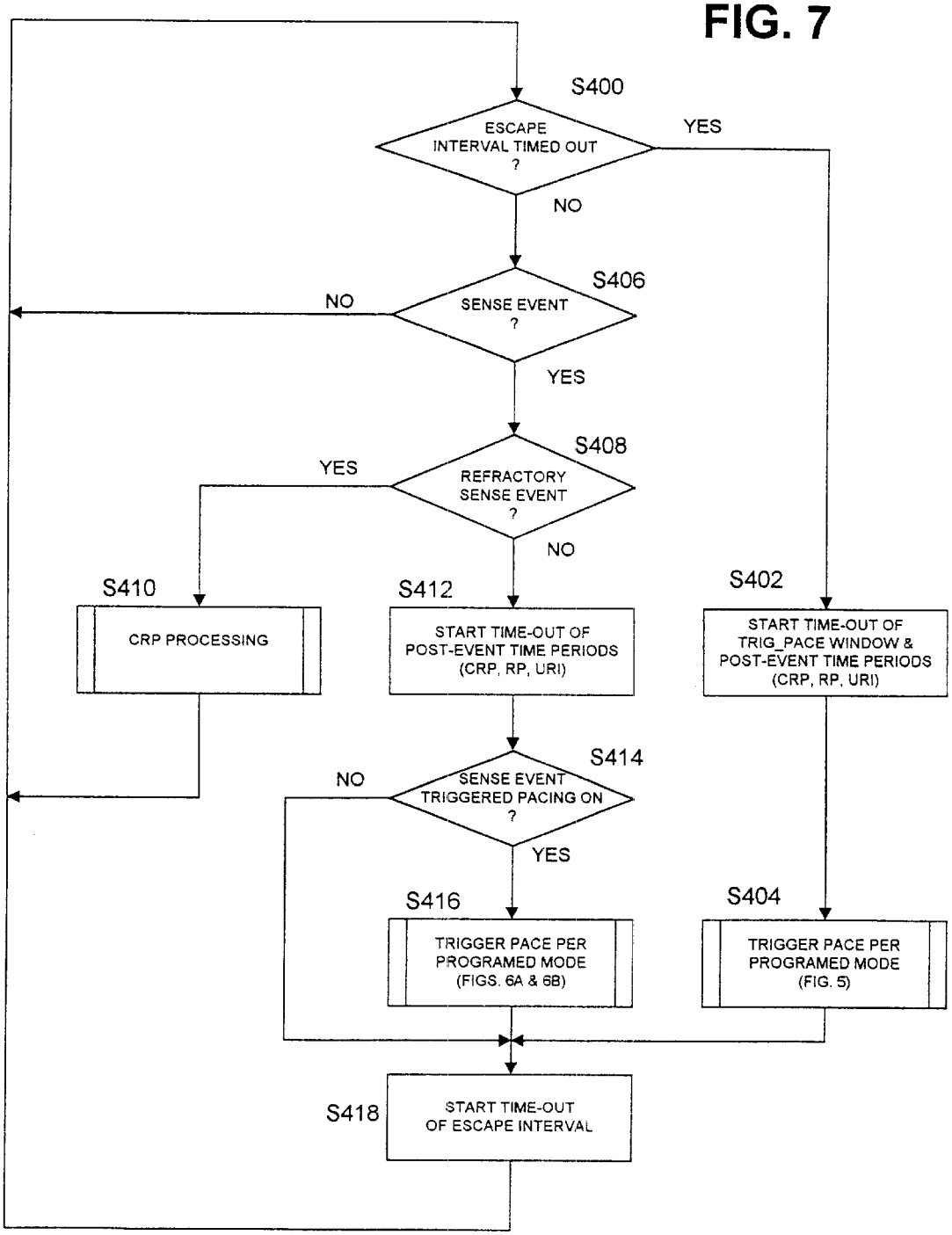
FIG. 7 is a comprehensive flow-chart illustrating the operating modes of the IPG circuitry of FIG. 3 in a variety of multi-site, single heart chamber and bi-atrial or bi-ventricular pacing modes in accordance with a further embodiment of the invention selectively employing steps of FIGS. 5 and 6A–6B therein.

For example, FIG. 7 is a comprehensive flow-chart illustrating the operating modes of the IPG circuit 300 of FIG. 3 in a variety of multi-site, single chamber or bi-atrial or bi-ventricular pacing modes in accordance with a further embodiment of the invention selectively employing steps of FIGS. 5 and 6A–6B therein. Thus, it will be assumed, for example, that the AV synchronous pacing DDD(R) mode is changed to an atrial or ventricular demand, and triggered pacing mode. When FIGS. 5 and 6A–6B are incorporated into steps of FIG. 7 as described below, it will be understood that references to the ventricles (V) in those flow chart steps are appropriate to the bi-ventricular pacing system and method. However, references to the atria (A) can be substituted for the references to the ventricles (V) in those flow chart steps for an understanding of a bi-atrial pacing system and method.

Moreover, the references to "RV" and "LV" can be changed to "first site" and "second site" in the context of multi-site pacing at spaced apart sites in a single heart chamber where first and second pace/sense electrodes are located. It is contemplated that the multi-site pacing system can include further pace/sense electrodes at further spaced apart sites in excess of two sites and corresponding additional pacing pulse output amplifier circuits and/or sense amplifiers coupled by leads to such pace/sense electrodes. For simplicity, the description of FIG. 7 is presented below in the context of a bi-chamber pacing system having pace/sense electrodes located at right and left heart chamber sites.

In step S400, the pacing escape interval started in step S418 from a prior R-SENSE or L-SENSE or previously delivered R-PACE or L-PACE (PACE1) is timing out. If the escape interval times out, then then the TRIG-PACE window and the post-event time periods, including a conditional refractory period (CRP), the URI and the refractory period (RP) are commenced and timed out in step S402. At the same time, at least a PACE1 pacing pulse is delivered to one of the RHC or LHC in step S404, and the escape interval is restarted in step S418. Step S404 is completed in accordance with the steps of FIG. 5 as described above to either deliver a PACE1 to the selected RHC or LHC pace electrodes or to deliver both PACE1 and PACE2 to both the selected RHC and LHC pace electrodes in a programmed right-to-left or left-to right sequence separated by a programmed P-P delay.

A sense EVENT that is output by any of the RHC or LHC or the trans-chamber sense amplifier during the escape interval in step S402 is characterized as a refractory or non-refractory sense EVENT in step S406. If it is a refractory sense EVENT, then the CRP processing steps are followed as described in the above-referenced application Ser. No. 09/439,244 to determine if it falls within or follows the time-out of the CRP and by how much the postevent time periods are to be continued or extended. In this case, the postevent time periods do not include a PVARP or PVABP, and only include a BP, RP, and URI plus the CRP. The refractory sense EVENT does not trigger delivery of any V-PACE pulses.

If a non-refractory SENSE occurs, then the CRP, the URI and the RP are commenced and timed out in step S412. At the same time, it is determined whether a triggered pacing mode is programmed on in step S414. If triggered pacing is off, then the escape interval is restarted in step S418 timed with the non-refractory sense EVENT detected in step S408, and the steps of FIGS. 6A and 6B are followed in step S416.

Triggered pacing proceeds if programmed on in step S416 and if the non-refractory SENSE falls outside the TRIG_PACE window as determined In steps S300 and S302 of FIG. 6A. If triggered pacing is programmed on, then it can be programmed to deliver PACE1 and PACE2 separated by the S/P-P delay in the predetermined right-to-left or left-to-right sequence in the manner of steps S300–S312 of FIG. 6A as described above.

The triggered pacing modes include delivering PACE1 alone to a programmed one of the RHC, regardless of where the sense EVENT was provided per step S316. Finally, delivery of PACE2 only can be programmed on, as determined in step S314. In that case, steps S314–S330 are followed as described above to deliver PACE2 to the other heart chamber than the heart chamber where the SENSE was provided by the sense amplifier coupled to it after time-out of a SENSE-PACE2 trigger delay.

The preceding specific embodiments are directed to RHC and LHC pacing in the predetermined sequence upon a sense event sensed in either or across the RHC and LHC. However, it will be understood that the present invention also embraces locating first and second pace/sense electrodes in a single heart chamber separated apart from one another along a physiologic depolarization pathway of a single heart chamber.

The preceding specific embodiments are illustrative of the practice of the invention. It is to be understood, therefore, that other expedients known to those of skill in the art or disclosed herein may be employed.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of such pacing systems that are not disclosed and are not necessary to the practice of the present invention. In addition, it will be understood that specifically described structures, functions and operations set forth in the above-listed, commonly assigned and co-pending patent applications can be practiced in conjunction with the present invention, but they are not essential to its practice.

In the following claims, means-plus-function clauses are intended to cover the structures described herein as performing the recited function and not only structural equivalents but also equivalent structures.

It is therefore to be understood, that within the scope of the appended claims, the invention may be practiced otherwise than as specifically described without actually departing from the spirit and scope of the present invention.

What is claimed is:

1. In a cardiac pacemaker, a method of delivering first and second pacing pulses to the heart comprising the steps of:
    locating first and second pace/sense electrodes at first and second spaced apart sites of the heart;
    sensing spontaneous cardiac depolarizations traversing the first pace/sense electrode and providing a first sense event signal;
    sensing spontaneous cardiac depolarizations traversing the second pace/sense electrode and providing a second sense event signal;
    upon provision of either a first or a second sense event signal, delivering a first pacing pulse to the first pace/sense electrode to pace the heart at the first site;
    upon provision of either a first or second sense event signal, commencing and timing out a triggered pacing delay; and
    at the time-out of the triggered pacing delay, delivering a second pacing pulse to the second pace/sense electrode to pace the heart at the second site,
    whereby a synchronized depolarization of the heart in a predetermined sequence is effected by the first and second pacing pulses regardless of whether the sense event signal originates from a spontaneous cardiac depolarization at the first or second spaced apart sites.

2. The method of claim 1, further comprising the step of:
    locating an indifferent pace/sense electrode in relation to the heart; and wherein:
    the sensing steps further comprise coupling a single sense amplifier to the first and second pace/sense electrodes to sense depolarizations traversing the first and second spaced apart sites and to provide the first and second sense event signals; and
    the step of delivering the first pacing pulse comprises delivering the first pacing pulse between the first pace/sense electrode and the indifferent pace/sense electrode; and
    the step of delivering the second pacing pulse comprises delivering the second pacing pulse between the second pace/sense electrode and the indifferent pace/sense electrode.

3. The method of claim 1, wherein the sensing steps further comprise:
    coupling a single sense amplifier to the first and second pace/sense electrodes for sensing depolarizations traversing one or the other of the first and second spaced apart sites and providing the first and second sense event signals.

4. A cardiac pacemaker for delivering first and second pacing pulses to the heart comprising:
    lead means for locating first and second pace/sense electrodes at first and second spaced apart sites of the heart;
    sensing means for sensing spontaneous cardiac depolarizations traversing the first pace/sense electrode and providing a first sense event signal and traversing the second pace/sense electrode and providing a second sense event signal;
    first pacing pulse generating means operable upon provision of either a first or a second sense event signal for delivering a first pacing pulse to the first pace/sense electrode to pace the heart at the first site;
    a triggered pacing delay timer operable upon provision of either a first or a second sense event signal for commencing and timing out a triggered pacing delay; and
    second pacing pulse generating means operable at the time-out of the triggered pacing delay for delivering a second pacing pulse to the second pace/sense electrode to pace the heart at the second site,
    whereby a synchronized depolarization of the heart in a predetermined sequence is effected by the first and second pacing pulses regardless of whether the sense event signal originates from a spontaneous cardiac depolarization at the first or second spaced apart sites.

5. The pacemaker of claim 4, wherein the sensing means further comprises a single sense amplifier coupled to the first and second pace/sense electrodes to sense depolarizations traversing one or the other of the first and second spaced apart sites and provide the first and second sense event signals.

6. The pacemaker of claim 4, further comprising:
    means for locating an indifferent pace/sense electrode in relation to the heart; and wherein:
    the sensing means further comprises a single sense amplifier coupled to the first and second pace/sense electrodes to sense depolarizations traversing the first and second spaced apart sites and provide the first and second sense event signals; and
    the first pacing pulse generating means is coupled to the indifferent pace/sense electrode and is operable to deliver the first pacing pulse between the first pace/sense electrode and the indifferent pace/sense electrode; and
    the second pacing pulse generating means is coupled to the indifferent pace/sense electrode and is operable to deliver the second pacing pulse between the second pace/sense electrode and the indifferent pace/sense electrode.

7. In a cardiac pacemaker, a method of sensing spontaneous cardiac depolarizations originating in right and left heart chambers and delivering right and left heart chamber pacing pulses to the right and left heart chambers for improving the hemodynamic efficiency of a sick heart suffering from conduction delays in conducting spontaneous or evoked depolarizations through the right and left heart chambers that compromise cardiac output, wherein said method comprises the steps of:

locating a right heart chamber pace/sense electrode at a right heart chamber site;

locating a left heart chamber pace/sense electrode at a left heart chamber site;

sensing spontaneous cardiac depolarizations traversing the right heart chamber site and providing a right heart chamber sense event signal;

sensing spontaneous cardiac depolarizations traversing the left heart chamber site and providing a left heart chamber sense event signal;

upon provision of either a right heart chamber sense event signal or a left heart chamber sense event signal, delivering a first pacing pulse to a predetermined one of the right heart chamber pace/sense electrode to pace the right heart chamber or the left heart chamber pace/sense electrode to pace the left heart chamber;

upon provision of either a right heart chamber sense event signal or a left heart chamber sense event signal, commencing and timing out a triggered pacing delay; and at the time-out of the triggered pacing delay, delivering a second pacing pulse to the other of the left heart chamber or the right heart chamber pace/sense electrodes to pace the other of the left heart chamber or the right heart chamber, whereby a synchronized depolarization of the right and left heart chambers in a predetermined right-to-left or left-to-right triggered pacing sequence is effected regardless of whether the sense event signal originates from a spontaneous cardiac depolarization in the right heart chamber or the left heart chamber.

8. The method of claim 7, further comprising the step of:

locating an indifferent pace/sense electrode in relation to the heart; and wherein:

the sensing step further comprises the step of coupling a single sense amplifier to the right and left heart chamber pace/sense electrodes to sense depolarizations traversing the right or left heart chamber sites;

the step of delivering the first pacing pulse comprises delivering the first pacing pulse between the predetermined one of the right or left heart chamber pace/sense electrodes and the indifferent pace/sense electrode; and the step of delivering the second pacing pulse comprises delivering the second pacing pulse between the predetermined other one of the right or left heart chamber pace/sense electrodes and the indifferent pace/sense electrode.

9. The method of claim 7, wherein the sensing step further comprises the step of:

coupling a single sense amplifier to the right and left heart chamber pace/sense electrodes for sensing depolarizations traversing one or the other of the right and left heart chamber sites.

10. The method of claim 7, wherein:

the step of locating a right heart chamber pace/sense electrode at a right heart chamber site comprises the step of advancing a bipolar pace/sense lead into the right heart chamber to locate a right heart chamber active pace/sense electrode and a right heart chamber indifferent pace/sense electrode in relation to the right heart chamber;

the step of locating a left heart chamber pace/sense electrode at a right heart chamber site comprises the step of advancing a unipolar pace/sense lead into a left heart chamber blood vessel to situate a left heart chamber active pace/sense electrode of the unipolar pace/sense lead adjacent to the left heart chamber; and the sensing step further comprises the step of coupling a single sense amplifier to the right and left heart chamber active pace/sense electrodes and the right heart chamber indifferent electrode for sensing right or left heart chamber depolarizations traversing one or the other of the right and left heart chamber sites.

11. The method of claim 10, wherein:

the step of delivering the first pacing pulse comprises delivering the first pacing pulse between the predetermined one of the right or left heart chamber active pace/sense electrodes and the right heart chamber indifferent pace/sense electrode; and the step of delivering the second pacing pulse comprises delivering the second pacing pulse between the predetermined other one of the right or left heart chamber active pace/sense electrodes and the right heart chamber indifferent pace/sense electrode.

12. The method of claim 7, wherein the right heart chamber comprises the right atrium and the left heart chamber comprises the left atrium.

13. The method of claim 7, wherein the right heart chamber comprises the right ventricle and the left heart chamber comprises the left ventricle.

14. The method of claim 7, wherein:

the step of delivering a first pacing pulse comprises delivering the first pacing pulse to the right heart chamber pace/sense electrodes to pace the right heart chamber: and the step of delivering a second pacing pulse comprises delivering the second pacing pulse to the left heart chamber pace/sense electrodes to pace the left heart chamber, whereby a synchronized depolarization of the right and left heart chambers in a predetermined right-to-left triggered pacing sequence is effected regardless of whether the sense event signal originates from a spontaneous cardiac depolarization in the right heart chamber or the left heart chamber.

15. The method of claim 7, wherein:

the step of delivering a first pacing pulse comprises delivering the first pacing pulse to the left heart chamber pace/sense electrodes to pace the left heart chamber: and the step of delivering a second pacing pulse comprises delivering the second pacing pulse to the right heart chamber pace/sense electrodes to pace the right heart chamber, whereby a synchronized depolarization of the right and left heart chambers in a predetermined left-to-right triggered pacing sequence is effected regardless of whether the sense event signal originates from a spontaneous cardiac depolarization in the right heart chamber or the left heart chamber.

16. A cardiac pacemaker for sensing spontaneous cardiac depolarizations originating in right and left heart chambers and delivering right and left heart chamber pacing pulses to the right and left heart chambers for improving the hemodynamic efficiency of a sick heart suffering from conduction delays in conducting spontaneous or evoked depolarizations through the right and left heart chambers that compromise cardiac output comprising:

a right heart chamber lead adapted to locate a right heart chamber pace/sense electrode at a right heart chamber site;

a left heart chamber lead adapted to locate a left heart chamber pace/sense electrode at a left heart chamber site;

sensing means coupled to the right heart chamber lead and providing a right heart chamber sense event signal upon sensing a spontaneous cardiac depolarization traversing the right heart chamber site and coupled to the left heart chamber lead and providing a left heart chamber sense event signal upon sensing a spontaneous cardiac depolarization traversing the left heart chamber site;

first pacing pulse generating means responsive to provision of either one of a right heart chamber sense event signal and a left heart chamber sense event signal for delivering a first pacing pulse to a predetermined one of the right heart chamber or the left heart chamber pace/sense electrodes to pace the right heart chamber or the left heart chamber;

a triggered pacing delay timer responsive to either one of a right heart chamber sense event signal and a left heart chamber sense event signal for commencing and timing out a triggered pacing delay; and second pacing pulse generating means responsive to the time-out of the triggered pacing delay for delivering a second pacing pulse to the other of the left heart chamber or the right heart chamber pace/sense electrodes to pace the other heart chamber at the site of that pace/sense electrode, whereby a synchronized depolarization of the right and left heart chambers in a predetermined right-to-left or left-to-right triggered pacing sequence is effected regardless of whether the sense event signal originates from a spontaneous cardiac depolarization in the right heart chamber or the left heart chamber.

17. The pacemaker of claim 16, further comprising:

means for locating an indifferent pace/sense electrode in relation to the heart; and wherein:

the sensing means further comprises a single sense amplifier coupled to the right and left heart chamber pacelsense electrodes to sense depolarizations traversing the right and left heart chamber sites;

the first right heart chamber pacing pulse generating means delivers the first pacing pulse between the predetermined one of the right or left heart chamber pace/sense electrodes and the indifferent pace/sense electrode; and the second pacing pulse generating means delivers the second pacing pulse between the predetermined other one of the right or left heart chamber pace/sense electrodes and the indifferent pace/sense electrode.

18. The pacemaker of claim 16, wherein the sensing means further comprises a single sense amplifier coupled to the first and second pace/sense electrodes for sensing depolarizations traversing one or the other of the right and left heart chamber sites.

19. The pacemaker of claim 16, wherein:

the right heart chamber lead comprises a bipolar pace/sense lead having a right heart chamber active pace/sense electrode and a right heart chamber indifferent pace/sense electrode advanced into the right heart chamber to locate the right heart chamber active pace/sense electrode and right heart chamber indifferent pace/sense electrode in relation to the right heart chamber;

the left heart chamber lead comprises a unipolar pace/sense lead having a left heart chamber active pace/sense electrode advanced into a left heart chamber blood vessel to situate the left heart chamber active pace/sense electrode adjacent to the left heart chamber; and the sensing means further comprises a single sense amplifier coupled to the right and left heart chamber active pace/sense electrodes and the right heart chamber indifferent pace/sense electrode for sensing right or left heart chamber depolarizations traversing one or the other of the right and left heart chamber sites.

20. The pacemaker of claim 19, wherein:

the first pacing pulse generating means delivers the first pacing pulse between the predetermined one of the right or left heart chamber active pace/sense electrodes and the right heart chamber indifferent pace/sense electrode; and the second pacing pulse generating means delivers the second pacing pulse between the predetermined other one of the right or left heart chamber active pace/sense electrodes and the right heart chamber indifferent pace/sense electrode.

21. The pacemaker of claim 16, wherein the right heart chamber comprises the right atrium and the left heart chamber comprises the left atrium.

22. The pacemaker of claim 16, wherein the right heart chamber comprises the right ventricle and the left heart chamber comprises the left ventricle.

23. The pacemaker of claim 16, wherein:

the first pacing pulse generating means delivers the first pacing pulse to the right heart chamber pace/sense electrodes to pace the right heart chamber: and the second pacing pulse generating means delivers the second pacing pulse to the left heart chamber pace/sense electrodes to pace the left heart chamber, whereby a synchronized depolarization of the right and left heart chambers in a predetermined right-to-left triggered pacing sequence is effected regardless of whether the sense event signal originates from a spontaneous cardiac depolarization in the right heart chamber or the left heart chamber.

24. The pacemaker of claim 16, wherein:

the first pacing pulse generating means delivers the first pacing pulse to the left heart chamber pace/sense electrodes to pace the left heart chamber: and the second pacing pulse generating means delivers the second pacing pulse to the right heart chamber pace/sense electrodes to pace the right heart chamber, whereby a synchronized depolarization of the right and left heart chambers in a predetermined left-to-right triggered pacing sequence is effected regardless of whether the sense event signal originates from a spontaneous cardiac depolarization in the right heart chamber or the left heart chamber.

25. A pacemaker for sensing spontaneous cardiac depolarizations in right and left heart chambers and delivering right and left heart chamber pacing pulse to the right and left heart chamber for improving the hemodynamic efficiency of a sick heart suffering from conduction delays in conducting spontaneous or evoked depolarizations through the right and left heart chambers that compromise cardiac output comprising:

a unipolar pace/sense lead adapted to be advanced into a left heart chamber blood vessel to situate a left heart chamber active pace/sense electrode of the unipolar pace/sense lead adjacent to the left heart chamber;

a bipolar pace/sense lead adapted to be advanced into the right heart chamber to locate right heart chamber pace/sense electrodes comprising a right heart chamber active pace/sense electrode and a right heart chamber indifferent pace/sense electrode in relation to the right heart chamber; and a pacing pulse generator comprising a pulse generator housing supporting a remote indifferent pace/sense electrode and enclosing circuitry comprising:

right heart chamber sensing means for sensing right heart chamber spontaneous cardiac depolarizations across the right heart chamber active and indifferent pace/sense electrodes and providing a right heart chamber sense event signal;

left heart chamber sensing means for sensing left heart chamber spontaneous cardiac depolarizations across left heart chamber pace/sense electrodes comprising the left heart chamber active pace/sense electrode and one of the remote indifferent pace/sense electrode and the right heart chamber indifferent pace/sense electrode for providing a left heart chamber sense event signal;

a triggered pacing delay timer responsive to provision of either one of a right heart chamber or a left heart chamber sense event signal for commencing and timing out a triggered pacing delay;

pacing pulse generating means responsive to provision of either one of a right heart chamber sense event signal or a left heart chamber sense event signal for delivering a first pacing pulse to a predetermined one of the right heart chamber pace/sense electrodes and the left heart chamber pace/sense electrodes and responsive to the time-out of the triggered pacing delay for delivering a second pacing pulse to the other of the right heart chamber pace/sense electrodes and the left heart chamber pace/sense electrodes, whereby a synchronized depolarization of the right and left heart chambers in a predetermined right-to-left or left-to-right triggered pacing sequence is effected upon provision of either one of a right heart chamber or a left heart chamber sense event signal.

26. The pacemaker of claim 25, wherein the right heart chamber comprises the right atrium and the left heart chamber comprises the left atrium.

27. The pacemaker of claim 21, wherein the right heart chamber comprises the right ventricle and the left heart chamber comprises the left ventricle.

\* \* \* \* \*